United States Patent [19]

Brennan

[11] Patent Number: 4,950,280
[45] Date of Patent: Aug. 21, 1990

[54] NASAL TAMPON HAVING A COUNTER WEIGHT

[76] Inventor: H. George Brennan, 1137 Granville, Newport Beach, Calif. 92660

[21] Appl. No.: 227,505

[22] Filed: Aug. 2, 1988

[51] Int. Cl.$^5$ ............................................. A61M 31/00
[52] U.S. Cl. ..................................... 606/196; 604/54; 604/1
[58] Field of Search .................. 604/1, 54, 904, 358, 604/359, 43; 128/325, 326, 341, 342; 606/191, 192, 196

[56] References Cited

U.S. PATENT DOCUMENTS

| 6,796 | 10/1849 | Haile . | |
|---|---|---|---|
| 1,235,095 | 7/1917 | Beck . | |
| 1,766,341 | 6/1930 | Kulik . | |
| 2,179,964 | 11/1939 | Stevens . | |
| 2,215,126 | 9/1940 | McMillin . | |
| 2,265,387 | 12/1941 | McMillin | 128/148 |
| 2,490,168 | 12/1949 | Strauss | 128/269 |
| 2,493,326 | 1/1950 | Trinder | 128/325 |
| 2,647,515 | 8/1953 | Pollock et al. | 128/325 |
| 2,691,985 | 10/1954 | Newsom | 128/342 |
| 2,847,997 | 8/1958 | Tibone | 128/325 |
| 3,049,125 | 8/1962 | Kirkowitsch | 128/325 |
| 3,420,237 | 1/1969 | Fortay | 128/323 |
| 3,452,752 | 7/1969 | DeCrescenzo | 604/904 |
| 3,516,407 | 6/1970 | Ruggero | 128/325 |
| 3,570,494 | 3/1971 | Gottschalk | 128/325 |
| 3,766,924 | 10/1973 | Pidgeon | 128/325 |
| 3,850,176 | 11/1974 | Gottschalk | 128/325 |
| 3,884,241 | 5/1975 | Walker | 128/325 |
| 4,030,504 | 6/1977 | Doyle | 128/325 |
| 4,233,025 | 11/1980 | Laison et al. | 604/1 |
| 4,338,941 | 7/1982 | Payton | 168/342 |
| 4,568,326 | 2/1986 | Rangaswamy | 604/1 |
| 4,606,346 | 8/1986 | Berg . | |
| 4,883,465 | 11/1989 | Brennan | 604/43 |

Primary Examiner—Jerome L. Kruter
Attorney, Agent, or Firm—Knobbe, Martens, Olson & Bear

[57] ABSTRACT

An improved nasal tampon for controlling and arresting hemorrhaging comprises an absorptive member, shaped to fit the gross contours of the nasal fossa, which is easily inserted in and removable from the nasal cavity. Affixed to one end of the tampon is a length of cord, having a weighted member appended thereto. The weighted member serves as a counter balance to aid in maintaining the tampon in place so as not to interfere with normal respiration through the mouth.

In an alternative embodiment, the tampon is equipped with a drainage conduit, connected to a source of suction, so as to aspirate blood from the nasal cavity. In a further alternative embodiment, a breathing conduit is provided to enable the patient to breathe through the nose when the device is operatively inserted.

16 Claims, 3 Drawing Sheets

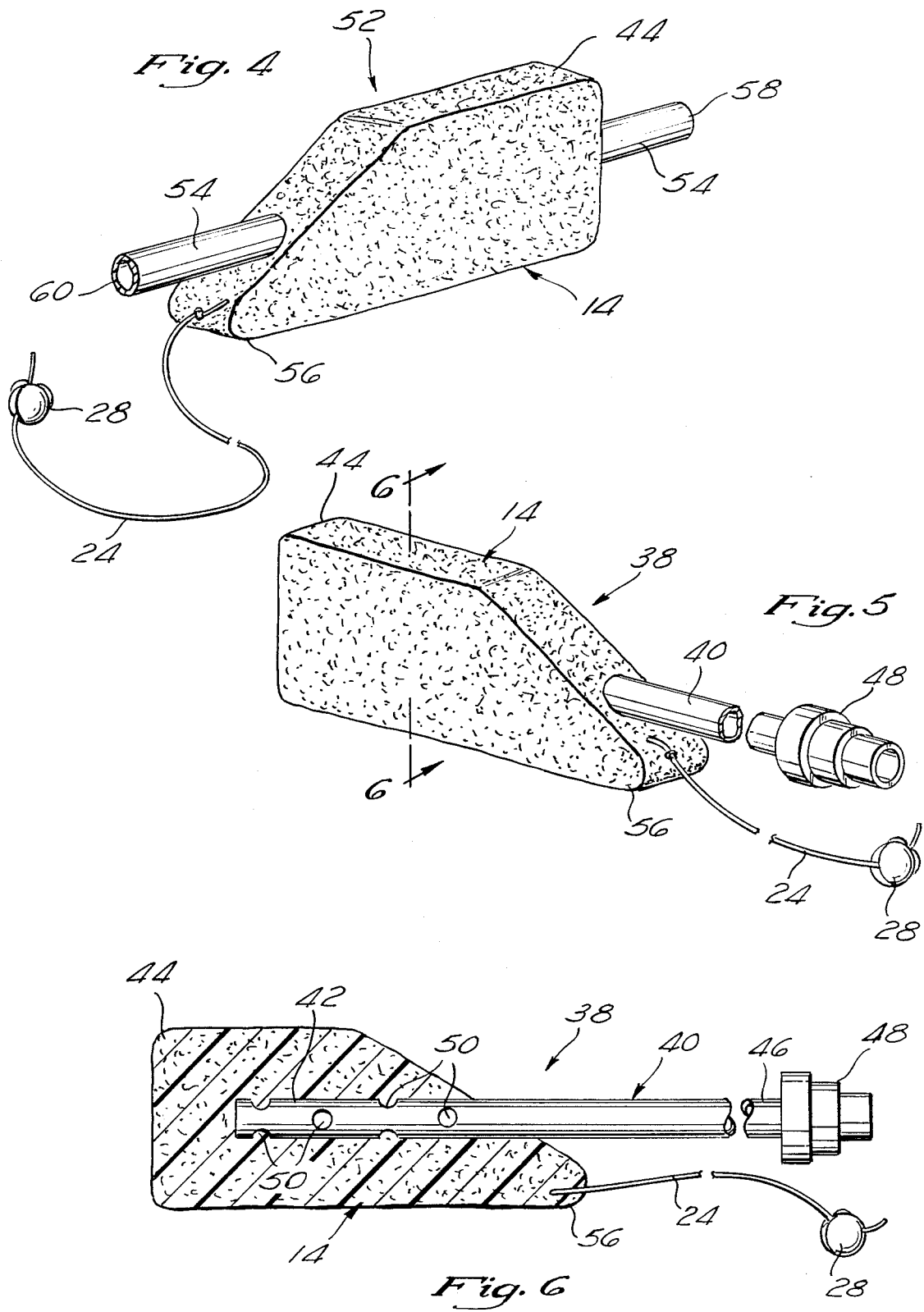

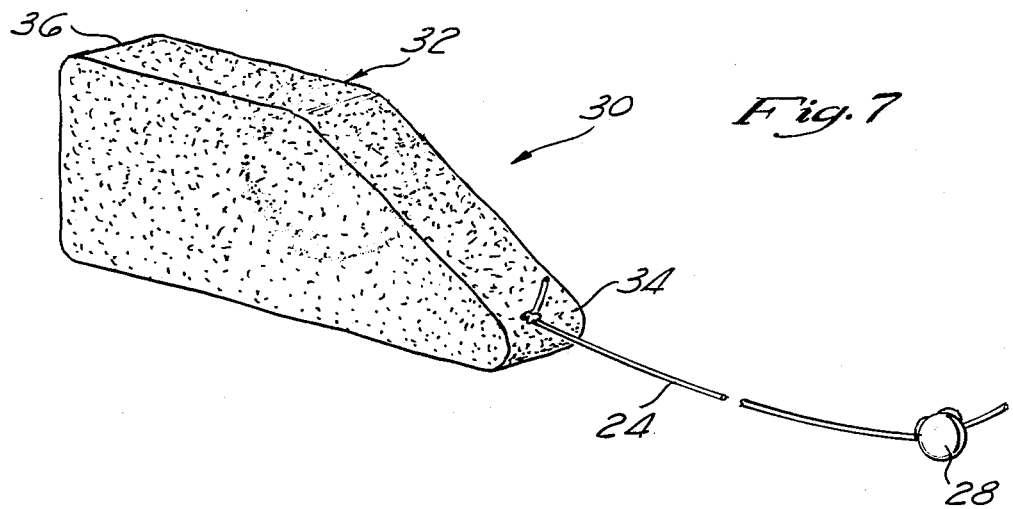
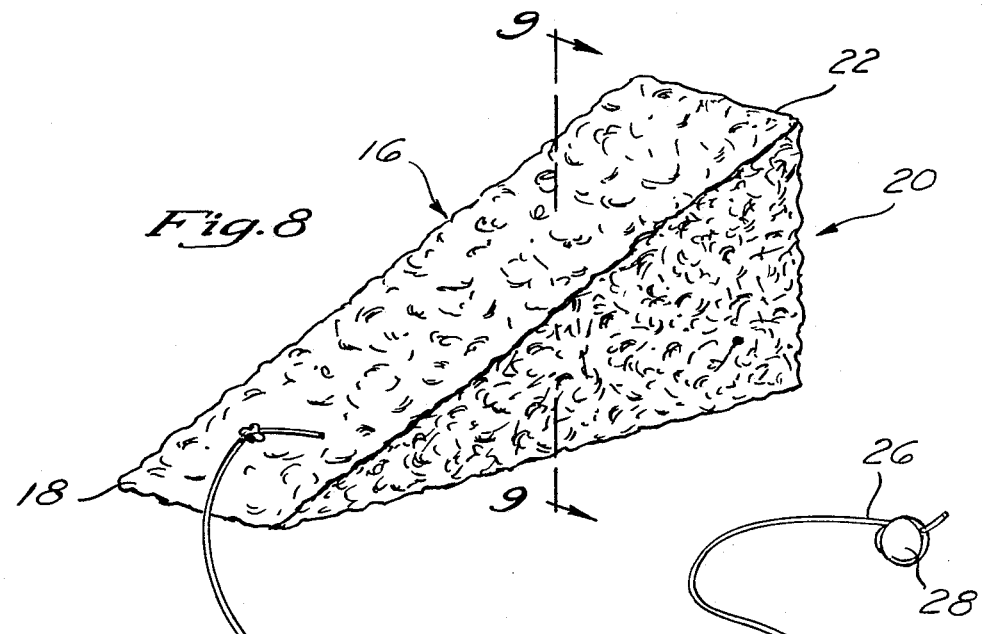
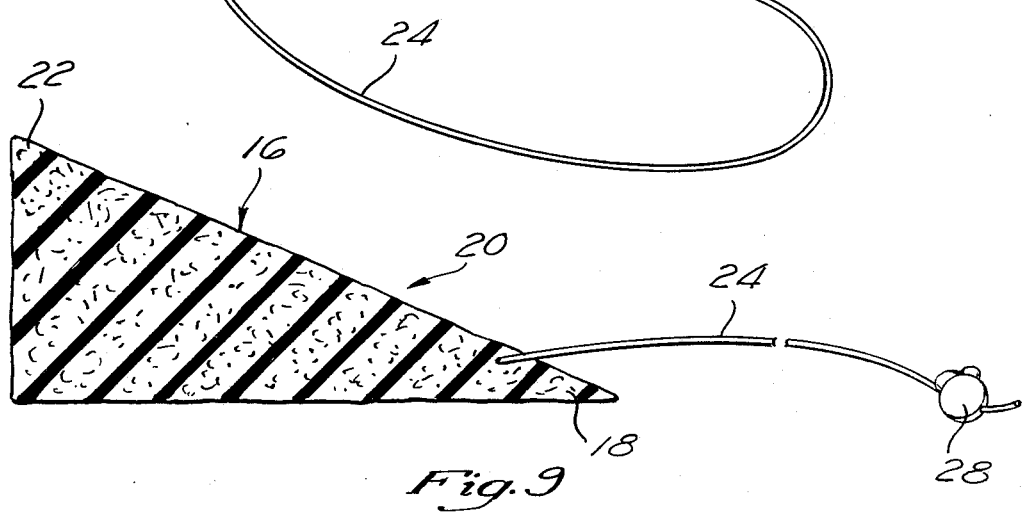

NASAL TAMPON HAVING A COUNTER WEIGHT

BACKGROUND OF THE INVENTION

This invention relates generally to nasal packing devices, and more particularly to an improved nasal tampon, designed to control nasal hemorrhaging.

Epistaxis, or nasal hemorrhaging which requires packing of the nose is quite a common phenomenon, as the nasal cavity houses branches of several major arteries near its surface. Traditionally, nasal hemorrhages have been arrested by forcing a plurality of gauze cylinders, or other absorptive material, into the nasal cavity one after the other, until sufficient pressure is created to provide a nasal hemostat. The nasal packing procedure is a quite involved, delicate process. The manipulation of the medical packing material into the posterior chamber of the nasal cavity to supply adequate pressure therein to relieve and eliminate bleeding is extremely time consuming, and often painful for the patient. Further, the packing of the posterior chamber of the nasal cavity is fraught with the disadvantage that the packing material easily slips from its intended area, blocking the larynx and throat opening of the patient, which can hamper the patient's breathing. In addition, the removal of nasal packings of this type is exceedingly awkward and time-consuming, not to mention uncomfortable if not painful to the patient.

More recently, catheter-like devices, having inflatable cuffs have been employed to arrest nasal hemorrhaging. Devices of this nature are inserted through the anterior nares in a deflated state, and then inflated within the nasal cavity to exert pressure on the area of bleeding and thereby arrest nasal hemorrhaging. Typically, such inflatable cuffs require relatively high inflation pressures which may severely damage the tender mucosal membrane by prolonged contact therewith.

Furthermore, the continuous excessive pressure associated with either of these types of devices tends to create congestion in the eyes and other adjacent parts which often produce nearly intolerable conditions.

SUMMARY OF THE INVENTION

The present invention provides a nasal tampon, of novel design, shaped to fit the gross contours of the nasal fossa, which is easily inserted in and removed from the nasal cavity.

Advantageously, the nasal tampon of the present invention is disposable, exceedingly simple in construction, and relatively inexpensive to manufacture.

A significant feature of the nasal tampon of the present invention is that it does not exert an excessive amount of pressure within the nasal cavity, yet has sufficient absorptivity to control nasal hemorrhaging.

In an alternative embodiment, a breathing conduit projects through the longitudinal center of the tampon to enable the patient to breathe through the nose while the device is operatively inserted.

In a further alternative embodiment, an aspirating device, connected to a source of suction, is provided within the body of the tampon to suction out blood, mucous and other fluids present in the nasal cavity. This eliminates the need for repeated removal and replacement of the tampon, as the aspirating device prevents the tampon from exceeding its absorptive capacity.

In yet another alternative embodiment, both the breathing conduit and the aspirating device are provided in the tampon. This alternative embodiment enables the tampon to be operatively installed for a prolonged period of time, with minimal discomfort to the patient.

The objects and other advantages of the present invention will become apparent from the ensuing detailed description, considered together with the appended drawings.

BRIEF DESCRIPTION OF THE DRAWINGS

FIG. 4 is a perspective view of an alternative embodiment of an improved nasal tampon consistent with the present invention;

FIG. 5 is a perspective view of a second alternative embodiment of an improved nasal tampon;

FIG. 6 is a cross-sectional view of the embodiment depicted in FIG. 5, taken along line 6—6;

FIG. 7 is a perspective view of a third alternative embodiment of the improved nasal tampon of the present invention;

FIG. 8 is a fourth alternative embodiment of the improved nasal tampon of the present invention; and FIG. 9 is a cross-sectional view of the nasal tampon depicted in FIG. 8, taken along line 9—9.

DETAILED DESCRIPTION OF THE PREFERRED EMBODIMENT

Figure 1:
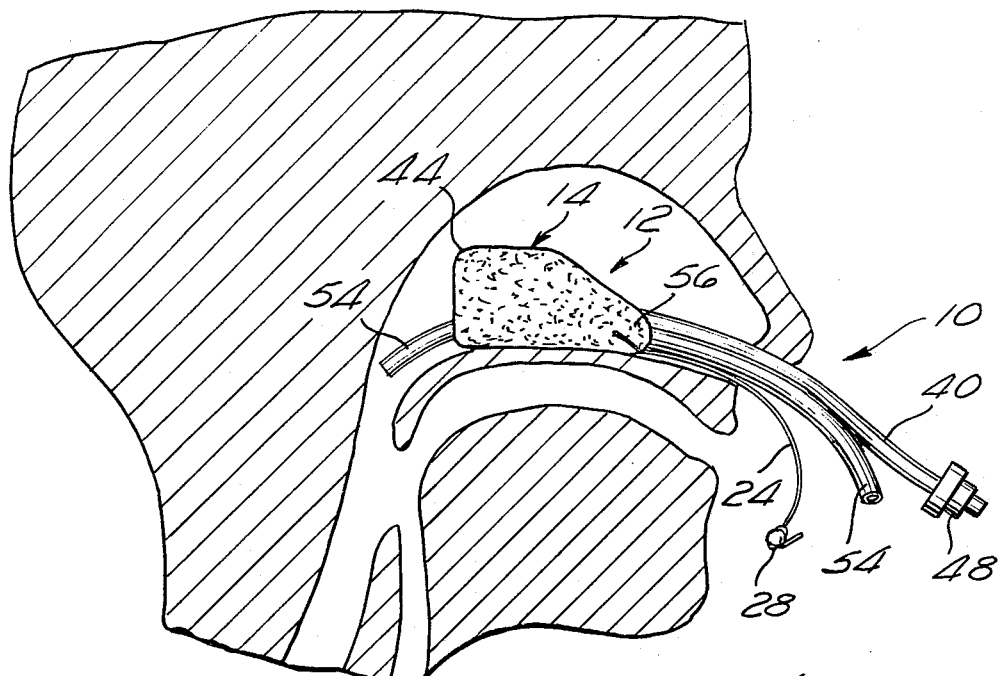
FIG. 1 is a diagrammatical view of a human head illustrating a nasal cavity and a preferred embodiment of the improved nasal tampon of the present invention, operatively installed within the nasal cavity.

Referring now to the drawings in detail, wherein like reference numerals designate like elements throughout the several views thereof, there is shown generally at 10 in FIG. 1, a nasal tampon embodying the present invention in a preferred form, positioned within a nasal cavity 12. As depicted in the drawings, the nasal tampon of the present invention generally comprises an absorptive member 14, shaped to fit the gross contour of the human nasal fossa.

As illustrated in FIG. 8, the nasal tampon of the present invention, in its simplest form, comprises a substantially triangular shaped sponge 16. Advantageously, the proximal end 118 of the tampon 20 has a smaller cross-sectional area than the distal end 22. Secured to the proximal end 18 of the tampon 20 is a length of cord 24, or other string-like member. At the other end 26 of the cord 24 is a weighted member 28, or shot. As illustrated by FIG. 9, the sponge 16 is of ordinary porous construction. The resilient qualities of the sponge 16 make the tampon 20 readily collapsible for easy insertion into the nasal cavity 12, and readily expandable once properly positioned therein. The weighted shot 28 acts as a counterbalance for the tampon and serves to prevent the tampon 20 from slipping from its intended area, so as to maintain the throat opening of the patient open to allow normal respiration through the mouth. Further, the cord 24 enables the physician to remove the tampon 20 without the use of forceps.

Another tampon embodiment 30, shown in FIG. 7, comprises an absorptive member 32, exhibiting a tapered proximal end 34 which has a smaller cross-sectional area than the distal end 36. A length of cord 24 and weighted shot 28 are attached to the proximal end 34 of the absorptive member 32, in the same manner as that described above. Unlike the common sponge 16 used in connection with the embodiment of FIG. 8, the absorptive member 32 of the tampon 30 shown in FIG. 7 is a MEROCEL (registered trade Mark) type sponge, as commercially available from and manufactured by American Coporation, Mystic, California Tampons constructed in accordance with this invention using the MEROCEL (registered trade Mark) absorptive member 32 exhibit generally superior absorptive capabilities to tampons made from the more common type of sponge. Either of these embodiments are particularly adapted for controlling the simplest of nasal hemorrhages, for example, a nose bleed.

For nasal hemorrhages involving more profuse bleeding, the tampon embodiment 38, depicted in FIGS. 5 and 6, is provided with a drainage conduit 40, adapted for connection to a source of suction (not shown). The distal end 42 of the drainage conduit 40 is enveloped by the absorptive member 14 through the longitudinal center thereof, without penetrating the distal end 44 of the absorptive member 14. The proximal end 46 of the drainage conduit 40 is equipped with a coupling device 48, integrally connected thereto. The coupling device 48 provides a means by which the drainage conduit 40 may be connected to a source of suction (not shown), so as to expel blood, mucous and other fluids from the absorptive member 14, thereby increasing the absorptive properties thereof.

As best shown in FIG. 6, the drainage conduit 40 includes a plurality of influent ports 50 which are completely encircled by the absorptive member 14. In this embodiment, the absorptive member 14 not only functions in an absorptive capacity, but also acts to prevent the surrounding nasal tissue from being inadvertently suctioned into the influent ports 50 of the drainage conduit 40. Additionally, when the drainage conduit 40 is connected to a source of suction, the absorptive member 14 evenly distributes the vacuum suction throughout its entire surface area. Accordingly, when bleeding is profuse, the drainage conduit 40 continuously suctions blood, etc. from the absorptive member 14, so as to enhance the absorptivity thereof.

A breathing conduit 54 is incorporated into the tampon embodiment 52. As shown, conduit 54 extends through the tampon 52, along its longitudinal center, out both the proximal and distal ends 56, 44, respectively. When the tampon 52 is inserted in the nasal cavity 12, the distal end 58 of the breathing conduit 54 extends into the nasopharyngeal passageway, so as to enable the patient to continue breathing through the nostril in which the tampon 52 is installed. This is particularly advantageous when both nostrils require packing. The proximal end 60 of the breathing conduit 54 is advantageously located outside the nasal cavity, so as to insure that the patient does not inadvertently aspirate blood while breathing through the conduit 54.

Figure 2:
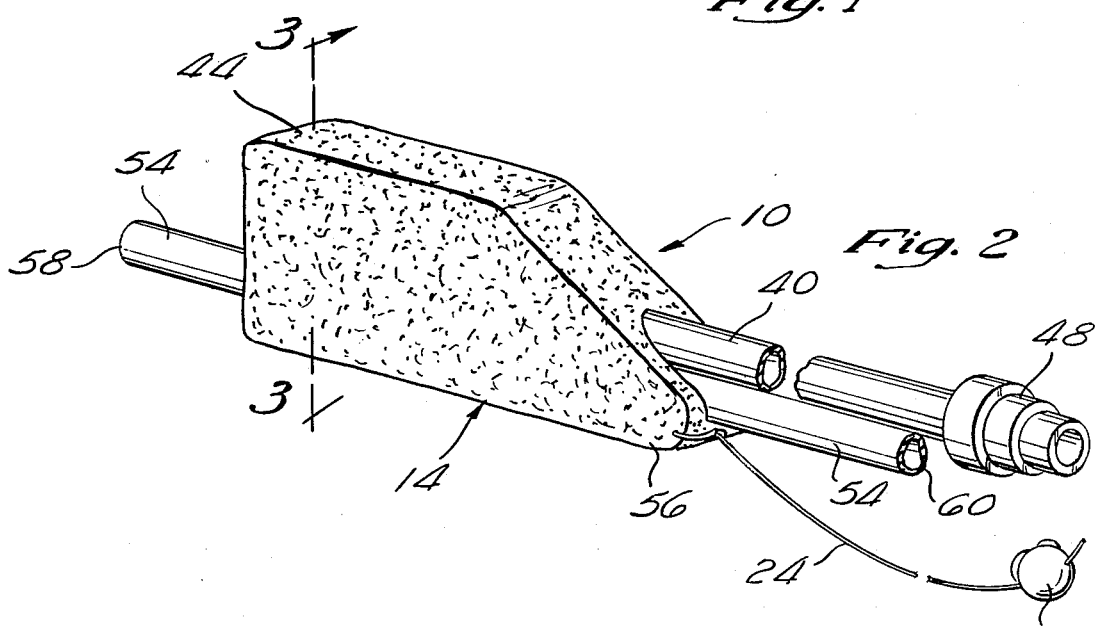
FIG. 2 is a perspective view of the nasal tampon depicted in FIG. 1.
Figure 3:
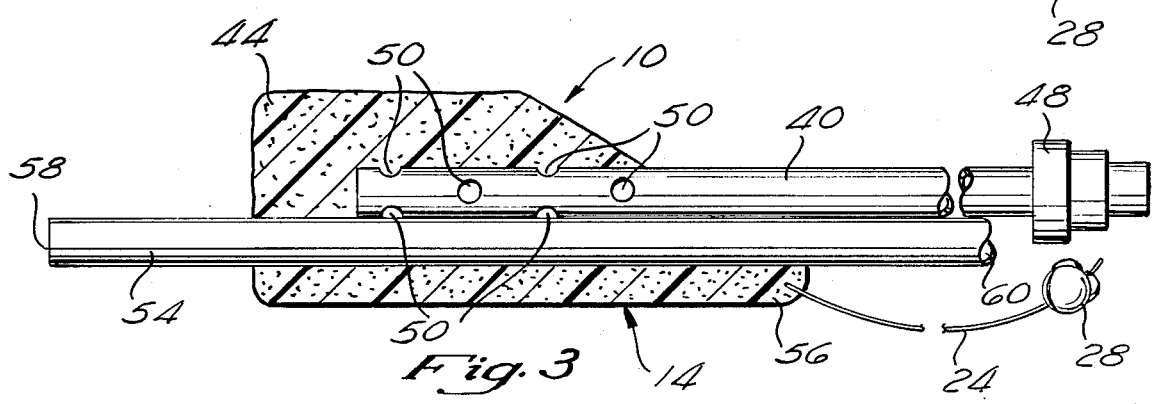
FIG. 3 is a cross-sectional view of a preferred embodiment of the nasal tampon of the present invention, taken along line 3—3 of FIG. 2.

Tampon 10 illustrated in either of FIGS. 1, 2 or 3, is the preferred embodiment. This tampon 10 is equipped with an absorptive member 14, having a length of cord 24 with a weighted shot 28 appended thereto, suitably attached to one end 56 of the absorptive member 14, a drainage conduit 40, encircled by, but not completely projecting through the absorptive member 14, and a breathing conduit 54 which does extend all the way through the absorptive member 14. This embodiment is particularly useful when the device 10 is to be operatively inserted within the nasal cavity 12 for prolonged periods of time. It has been found that such a combination is most comfortable for the patient, allows normal breathing through the nose, and efficiently controls nasal hemorrhages.

Preferably, the drainage and breathing conduits 40, 54 are formed by injection molding. A material which is well adapted to construction of the conduits is Poly Vinyl Chloride (PVC), such as Firestone's EXON (registered trade Mark) No. 654 or Borden's VC-2605, made flexible with approximately 50% of a plasticizer, such as dioctyl phthalate. Any conventional inert plasticizer such as adipate plasticizers or other phthalate esters can also be used.

MANNER OF USE OF THE NASAL TAMPON

All of the above-described embodiments of the present invention are adapted for use as hemorrhage arrest and controlling devices. The above-described nasal tampons are suited to control any variety of nasal hemorrhages, from controlling a simple nose bleed to use during rhinoplasty or other reconstructive or corrective surgical procedures in the vicinity of the nose. The shape of the tampons, along with their absorptive capabilities leave sufficient working room in the frontal portion of the nose to enable a surgeon to perform such a surgical procedure.

Prior to inserting one of the nasal tampons into the nostril of a patient, it is often times desirable to line the tampon with a polymeric organic silicon compound which will prevent adherence of blood or other liquid matter thereto. Well suited for this purpose is a ZYLOCANE gel, which serves to lubricate the tampon as well as provide a local anesthetic to desensitize the area. The tampon is then inserted into the nasal cavity using forceps. If a drainage conduit 40 is to be employed, the coupling device 48 is connected to a source of suction, so as to evacuate the absorptive member and nasal cavity of excess blood, etc.

The flexible material with which the conduits 40, 54 are made allow the conduits to follow the normal front to back curvature of the nasal cavity, to facilitate insertion. After hemorrhaging has been arrested, the tampon may be slowly guided out of the nasal cavity 12 by steadily and continuously exerting a slight pulling force on the cord 24, in a direction away from the anterior nares.

Although certain specific embodiments of the invention have been shown and described, it should be readily apparent that many modifications are possible. The invention is therefore not intended to be restricted to the exact showing of the drawings and description thereof, but is considered to include reasonable and obvious equivalents.

What is claimed is:

1. An improved nasal tampon for controlling and arresting nasal hemorrhaging, said tampon having a proximal end and substantially eliminating the risk of slippage from the nasal cavity into the pharynx once it is installed, said nasal tampon comprising:

an absorptive member, having a proximal portion, sized and shaped to fit the gross contours of the nasal fossa, said absorptive member readily compressible for easy insertion through the anterior nares of a patient, and resilient to expand once positioned within the nasal cavity;

counterweight means flexibly attached to said proximal end of said absorptive a member, to pass through the nares and provide sufficient force in a direction externally which would remove said nasal tampon from the nasal cavity, to prevent slippage thereof into the larynx of the patient to maintain the throat opening clear and allow continued normal respiration through the mouth.

2. An improved nasal tampon, as defined by claim 1, additionally comprising:
a flexible element attached between said counterweight means and said proximal portion.

3. An improved nasal tampon, as defined by claim 2, wherein said absorptive member is sized so that when said absorptive member is inserted into the nasal cavity, at least the frontal one-third of the nasal cavity is left clear for said nasal procedure.

4. An improved nasal tampon, as defined by claim 1, wherein said counterweight means comprises a drainage conduit, having one end disposed within the body of said absorptive member, and another end integrally connected to a coupling device, said drainage conduit having a plurality of influent ports near said end within said absorptive member so as to enable blood, mucous, and other fluids to be suctioned from said absorptive member when said coupling device is connected to a source of suction.

5. An improved nasal tampon, as defined by claim 4, wherein said absorptive member is mounted on said drainage conduit in a position which prevents soft tissue within the nasal cavity from being suctioned into said influent ports of said drainage conduit.

6. An improved nasal tampon, as defined by claim 4, wherein said absorptive member comprises a porous sponge which evenly distributes the vacuum force created by said suction over substantially the entire surface of said porous sponge.

7. An improved nasal tampon, as defined by either one of claims 1 or 4, further comprising a breathing conduit which extends through said absorptive member to allow normal breathing through the nostril in which said tampon is installed.

8. An improved nasal tampon, as defined by claim 1, wherein said absorptive member comprises a porous sponge.

9. An improved nasal tampon, as defined by claim 1, wherein said tampon is coated with a lubricant to prevent adherence of blood or other liquid matter thereto.

10. An improved nasal tampon, as defined by claim 9, wherein said lubricant is a gel.

11. A disposable nasal tampon having a proximal end, said nasal tampon controlling and arresting nasal hemorrhages and substantially eliminating the risk of slippage from the nasal cavity into the pharynx, comprising:

an absorptive member, sized and shaped to fit within the nasal fossa, and having a proximal portion, and;
counterweight means flexibly affixed to said proximal portion of said absorptive member to pass through the nares, said counterweight means providing sufficient force in a direction externally which would remove said nasal tampon from the nasal cavity to prevent said tampon from slipping into the patient's pharynx and interfering with normal respiration.

12. A disposable tampon, as defined by claim 11, wherein said absorptive member is readily compressible to ease insertion, and wherein a flexible member attaching said counterweight means to said proximal end of said absorptive member facilitates easy removal of said tampon once hemorrhaging has been arrested.

13. A disposable nasal tampon, as defined by claim 11, wherein said counterweight means comprises a flexible drainage conduit, having one end disposed within the body of said absorptive member and another end adapted for connection to a source of suction, said end within said body of said absorptive member exhibiting a plurality of influent ports for withdrawing fluid from said absorptive member to increase the absorptive capacity thereof.

14. A disposable nasal tampon, as defined by claim 13, further comprising a breathing conduit, extending through said tampon, to enable the patient to breathe through the nose when said tampon is in place.

15. A method of controlling and arresting any variety of nasal hemorrhages, from controlling a simple nose bleed to use during rhinoplasty or other reconstructive or corrective surgical procedures in the vicinity of the nose, comprising the steps of:
providing a tampon having a proximal end and a counterweight flexibly attached to said proximal end;
compressing said tampon for insertion in the nasal cavity through the anterior nares;
positioning said tampon within the nasal cavity to control nasal hemorrhaging but with said counterweight means extending through the nares and outside of the nasal cavity; and
using said counterweight means to provide force in a direction exterior of the nose to thwart slippage of said tampon into the larynx of the patient to maintain the throat opening clear and allow continued normal respiration through the mouth.

16. A method of controlling and arresting any variety of nasal hemorrhages, as defined by claim 15, wherein said tampon counterweight means includes a drainage conduit, further comprising the step of connecting said drainage conduit to a source of suction to evacuate the tampon and nasal cavity of blood, mucous, and other fluids present therein.

* * * * *